(12) United States Patent
Deane et al.

(10) Patent No.: US 7,841,343 B2
(45) Date of Patent: Nov. 30, 2010

(54) SYSTEMS AND METHODS FOR DELIVERING THERAPEUTIC GAS TO PATIENTS

(75) Inventors: Geoffrey Frank Deane, Goleta, CA (US); Brenton Alan Taylor, Kenwood, CA (US)

(73) Assignee: Inogen, Inc., Goleta, CA (US)

( * ) Notice: Subject to any disclaimer, the term of this patent is extended or adjusted under 35 U.S.C. 154(b) by 1122 days.

(21) Appl. No.: 11/147,409

(22) Filed: Jun. 6, 2005

(65) Prior Publication Data
US 2005/0274381 A1  Dec. 15, 2005

Related U.S. Application Data

(60) Provisional application No. 60/577,088, filed on Jun. 4, 2004.

(51) Int. Cl.
*A61M 11/00* (2006.01)
(52) U.S. Cl. .............................. 128/204.23; 128/204.18
(58) Field of Classification Search ............ 128/204.23, 128/204.18; 600/538
See application file for complete search history.

(56) References Cited

U.S. PATENT DOCUMENTS

| | | | |
|---|---|---|---|
| 4,823,788 A | 4/1989 | Smith et al. | |
| 4,971,049 A | 11/1990 | Rotariu et al. | |
| 4,986,269 A | 1/1991 | Hakkinen | |
| 5,603,315 A * | 2/1997 | Sasso, Jr. | 128/204.18 |
| 5,735,268 A * | 4/1998 | Chua et al. | 128/204.23 |
| 5,865,174 A | 2/1999 | Kloeppel | |
| 5,890,490 A | 4/1999 | Aylsworth et al. | |
| 6,186,142 B1 * | 2/2001 | Schmidt et al. | 128/204.23 |
| 6,626,175 B2 * | 9/2003 | Jafari et al. | 128/204.21 |
| 7,152,598 B2 * | 12/2006 | Morris et al. | 128/204.23 |

FOREIGN PATENT DOCUMENTS

WO  WO 2004/041073 A2  5/2004

OTHER PUBLICATIONS

Partial International Search Report for PCT/US2005/020132.

* cited by examiner

*Primary Examiner*—Steven O Douglas
(74) *Attorney, Agent, or Firm*—Knobbe, Martens, Olson & Bear LLP

(57) ABSTRACT

A system for delivering therapeutic breathing gas to patients is provided to deliver a variable bolus volume in response to the patient's breathing pattern. The system includes a gas source, a conserver between the gas source and the patient, a sensor which detects breaths by the patient and a controller which receives signals from the sensor and triggers delivery of gas boluses in accordance with predefined triggering parameters, with the controller determining the time elapsed since the last bolus was triggered and altering the triggering parameters as a function of the elapsed time.

12 Claims, 10 Drawing Sheets

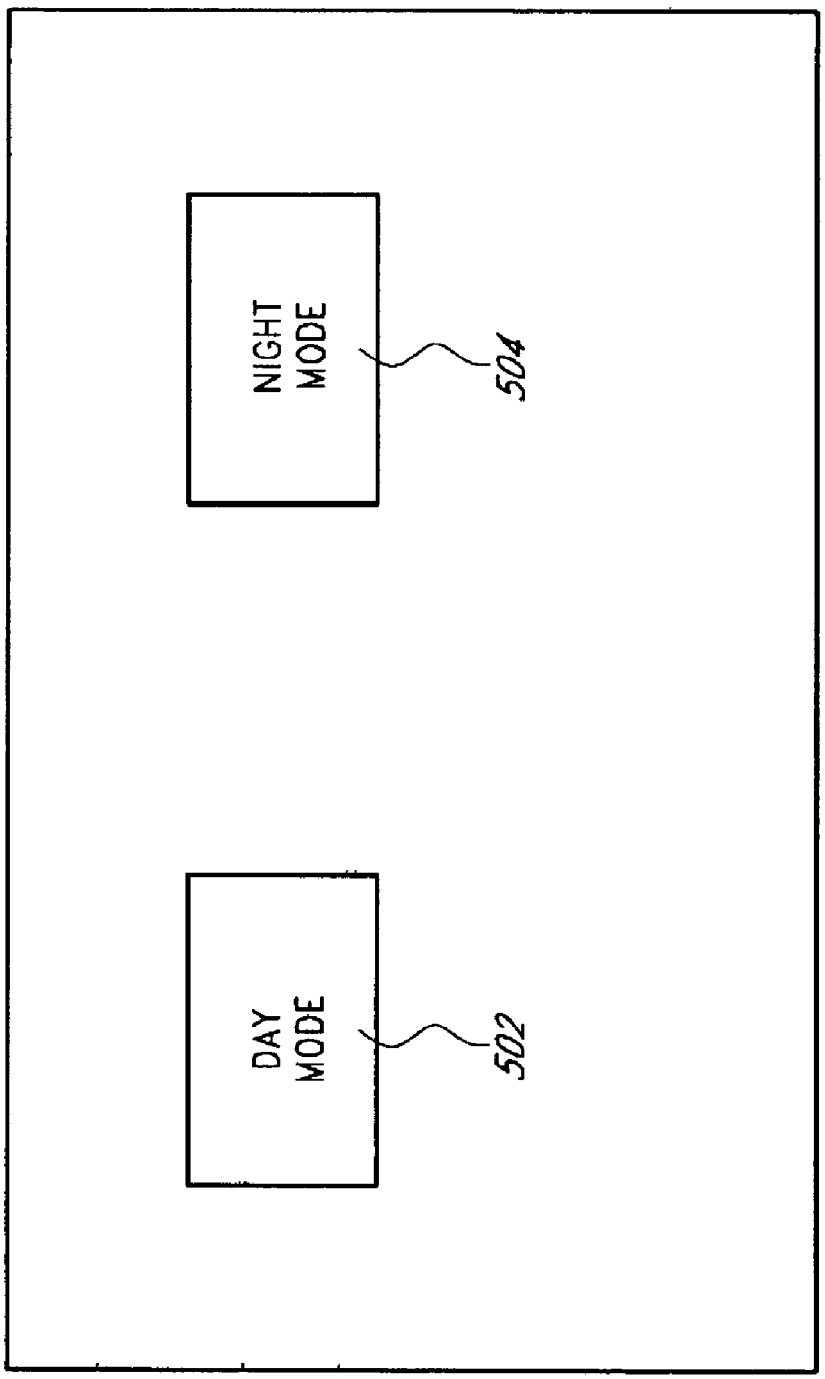

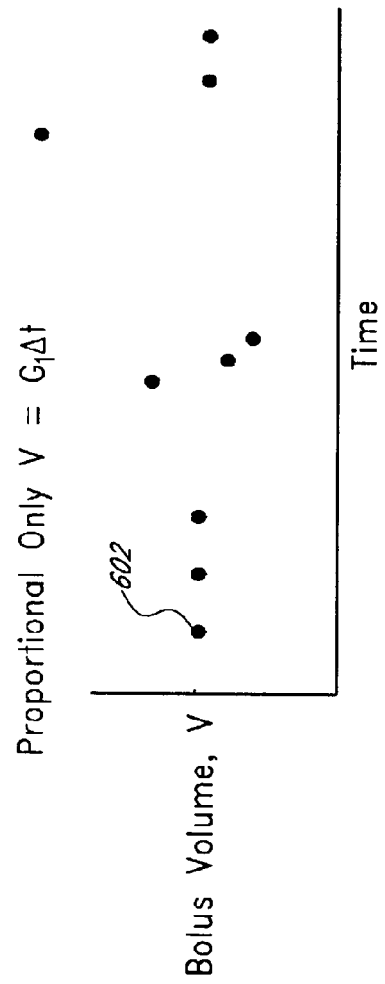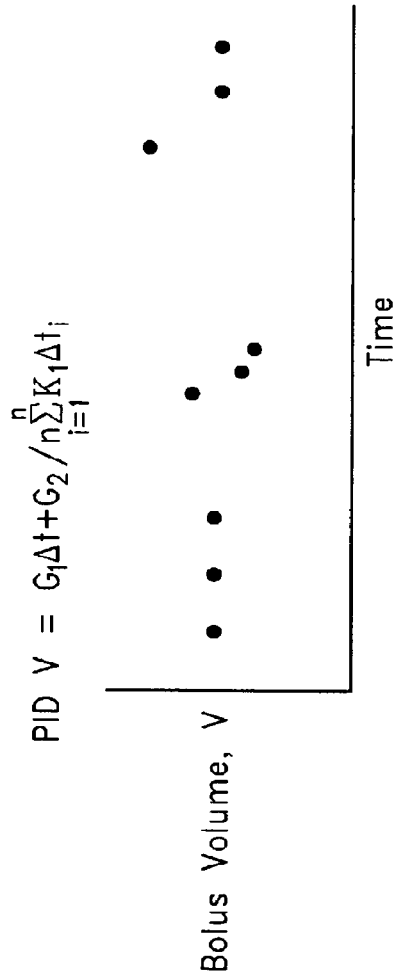

SYSTEMS AND METHODS FOR DELIVERING THERAPEUTIC GAS TO PATIENTS

RELATED APPLICATIONS

This Application claims the benefit of U.S. Provisional Patent Application Ser. No. 60/577,088, filed Jun. 4, 2004, which is hereby incorporated by reference in its entirety.

BACKGROUND OF THE INVENTION

1. Field of the Invention

This invention relates generally to systems and methods for delivering therapeutic gas to patients, and in particular, relates to such systems and methods in which the gas delivery is tailored to the patient's breathing pattern.

2. Description of the Related Art

The application of oxygen concentrators for therapeutic use is known, and many variants of such devices exist. A particularly useful class of oxygen concentrators is designed to be portable, allowing users to move about and to travel for extended periods of time without the need to carry a supply of stored oxygen. Such portable concentrators must be small and light to be effective. Oxygen concentrators in general are implicitly limited in terms of the rate at which they can deliver oxygen to the patient, but benefit because they are only duration-limited by their access to electric power. To make the portable concentrators small and light, the rate at which oxygen is concentrated by the device is further restricted. However, use of a device called a conserver, which is placed in the product line between the concentrator and the patient, mitigates this limitation.

The conserver, many designs of which are known in the art, senses a patient's breath demand, and responds by delivering a volume of oxygen-rich gas (known as a bolus) to the patient. This bolus, which is often significantly less than the total volume of a typical inhalation, is entrained in the breath's air intake, and mixes with the air, eventually reaching the lungs, esophagus, and respiratory cavities (nose and mouth). Approximately half of an inspiration enters the lungs, where oxygen is adsorbed. Elevated oxygen concentration in this volume result in greater transfer of the gas to the blood, which enhances the health of the patient. Because the lungs can only make use of oxygen in the volume that reaches them, it is important that the bolus be delivered during the portion of an inhalation that actually reaches the lungs. As this is typically the first fifty percent of a breath, the bolus should be delivered quickly, requiring that the bolus delivery start as rapidly as possible after the start of the patient's breathe. Quick delivery of the bolus allows smaller boluses to be delivered while still satisfying the patient's need for oxygen. Thus, conservers that deliver an effective therapeutic amount of oxygen in relatively small, short bursts, constitute a more efficient use of the concentrated product gas. This allows for the design of small, lightweight concentrators that are equally effective as the large continuous flow gas supplies.

Although one of the primary motivations behind small concentrators is to allow patient freedom and mobility, the cost of these devices makes it advantageous if the concentrator is a single solution, used 24 hours a day, for all of a patient's oxygen needs. In order to be so employed, it is desirable to maximize the concentrator's efficacy while a patient is sleeping. However, there is concern in the respiratory care field that conserver-based delivery of oxygen is not as effective as continuous flow gas supplies at maintaining patient blood oxygen saturation levels during sleep.

One cause for this nighttime desaturation concern surrounds the conserver's sensitivity, or the inhalation vacuum pressure (typically sensed through a nasal cannula) that results in a bolus delivery. In order to reduce false triggers (bolus delivery when no breath has occurred), breath detection, which is accomplished by measuring inhalation vacuum pressure typically through a nasal cannula, is set to a level corresponding to normal daytime breathing and activity patterns. If the pressure at which the conserver triggers a bolus is too low, normal activity may cause false firing, which can be disconcerting to patients and is ineffective oxygen therapy as much of this oxygen does not reach the lungs. However if the trigger pressure is too high, the conserver does not recognize a breath until a significant portion of it has already been inspired, which reduces the efficacy of the delivered bolus. Thus, it is desirable to have the conserver's breath sensitivity be as high as possible such that bolus delivery speed is accelerated, so long as this sensitivity remains low enough to avoid activity-induced false firing.

In addition, conserving devices typically deliver a predetermined volume of gas in response to patient breath demand. During sleep, the normal daytime trigger levels may be too high, and the associated bolus volumes may not be adequate to maintain required blood oxygen saturation levels. Moreover, during sleep, some patients are shallow and/or irregular breathers, such that nighttime breathing for these patients may not generate enough vacuum pressure to trigger bolus delivery. In some cases, due to irregular breathing patterns, the conserver may not detect every breath, resulting in breath skipping. In either of these cases, a bolus may not be triggered often enough to deliver enough oxygen to the patient over time. Many conservers are equipped with a breath detection or apnea alarm that notifies the user when no breath has been detected for some period. However, the alarm can awaken the sleeping patient, which makes use of the conserver not feasible.

Since most therapeutic gas systems deliver gas and sense patient breathing through a nasal cannula, patients who breathe through their mouths at night may never trigger bolus delivery. It is known within the respiratory care field that while patients are breathing through their mouths, they are entraining oxygen rich gas stored in the nasal passages with each inhalation. As such, large air supply systems simply deliver continuous flow to the nasal passages. However, continuous flow oxygen delivery, when not inhaled through the nose, may result in a cloud of oxygen-enriched gas around the face with oral inhalation entraining only some of this gas. As a result, the rate of oxygen delivery in these continuous flow oxygen systems often have to be increased during sleep to compensate for these inefficiencies in delivery.

Thus, it is apparent that new approaches to conserver-based delivery for sleep mode operation are desired in order to provide patients with the opportunity to use the small air concentrators 24 hours a day.

SUMMARY OF THE INVENTION

In one aspect, the preferred embodiments of the present invention provide an improved system for delivering therapeutic breathing gas, typically but not limited to oxygen from a concentrator, to a patient. The system generally includes a gas source, a conserver between the gas source and the patient, a sensor for detecting patient breath events and measuring the parameters of the breath events, and a processor and control elements for acquiring signals from the sensor and controlling the delivery of gas to the patient. Preferably, the gas is oxygen and the gas source is an oxygen concentrator. In one embodiment, the system supports at least one mode of operation such that the level of breath pressure detected by the sensor, which causes the processor and control elements to deliver a volume of gas to the patient, may be set to several different levels. In one implementation, the levels are user selectable. In another implementation, the different levels comprise two user selectable levels, representing a night mode and a day mode, wherein the actual values of each level is determined by the patient's caregiver.

In another embodiment, the system supports at least one mode of operation such that the level of sensitivity, or the minimum inhalation vacuum pressure required for the conserver to register a breath detection and to initiate bolus delivery in response, may be set to several different levels. In one implementation, the conserver may be adjusted to operate over a range of sensitivity levels. The sensitivity levels may be pre-set discrete values that are pre-selected. In another implementation, two operating modes are user selectable. The two operating modes can represent a night or sleep mode and a day or activity mode. The sensitivity of the conserver may be different in each mode to allow for different activity levels and breathing characteristics. The sensitivity level for each of the above modes may be either accessed through a simple user interface such that the patient may manually adjust the sensitivity. Alternatively, access to the sensitivity settings may be more difficult, designed such that the actual values are selected by the patient's caregiver.

In yet another embodiment, the system supports at least one mode of operation where a fixed volume of gas is automatically delivered to the patient at a fixed rate ("auto-firing mode"). In one implementation of this embodiment, a conserving device delivers boluses at a fixed bolus volume and a fixed rate such that the product of volume times the rate closely matches a desired volume flow delivery rate. In another implementation of this embodiment, the desired volume flow delivery rate matches the capacity of an oxygen concentrator to produce oxygen.

In yet another embodiment, the system supports at least one mode of operation such that the sensitivity varies in response to breathing characteristics. In this embodiment, the conserver controller may vary the threshold pressure signal at which breath detection occurs in response to other system parameters. In one implementation, the system supports at least one mode of operation such that:

the processor determines the average "breath period", or average time between successive bolus delivery events or breath detection events;

the processor and control elements ignore any vacuum pressure signals, for a first fraction of the breath period termed the "blind time" (the time required to deliver a bolus resulting from the first inhalation detection event may be a subset of this period);

the processor and control elements vary the breath detection threshold pressure signal at which gas delivery will occur from a high level to a low level during a second fraction of the breath period; and the processor and control elements hold the breath pressure level at the low level until a breath occurs.

The rate at which the breath detection threshold pressure signal decreased during the second fraction of the breath period may be linear. Alternatively, the rate of increase may follow an exponential function or other suitable functions.

In yet another embodiment, the system operates such that if no breath occurs after a preset time period, the system automatically delivers or auto-fires a volume of gas to the patient. The preset time period is referred to as "auto-fire time". In one implementation, this auto-fire bolus volume may be fixed, dependent only on user flow setting. In another implementation, this auto-fired bolus volume may vary in proportion to the elapsed time since the last bolus volume delivery was initiated, or in a manner reflecting a proportional-integral-derivative (PID) control method in response to a bolus delivery rate. In yet another implementation, the threshold pressure may continue to decrease until either a breath is detected or a bolus is automatically fired. In this implementation, the threshold pressure may linearly or asymptotically approach zero, or a value less than signal noise on the pressure sensor, resulting in an automatic bolus firing. In the event of automatically delivering a breath to the patient, the processor sets a shorter breath period than the previous breath period for use in determining the auto-fire time for the next breath cycle. When combined with other embodiments, this shorter breath period may also result in changes in threshold pressure ramp rates or other characteristics based on time. In the event that the conserver auto-fires repeatedly, successively reducing the breath period used in controlling the sensitivity and/or other parameters for each subsequent breath, the breath period approaches some minimum value. This value is preferably longer than the blind time, so as to allow some period during each breath period where a breath may be detected. The rate at which the breath period is reduced may be linear, exponential, or may asymptotically approach this minimum value.

In yet another embodiment, the system supports at least one mode of operation such that the system auto-fires after some period of time if no breath are detected. In the event of auto-firing to the patient, the processor reduces the threshold pressure for breath detection during the subsequent delivery cycle. In another implementation, the processor reduces both the threshold pressure and the breath period simultaneously, with each varying as described in above embodiments.

In yet another embodiment, the system supports at least one mode of operation such that the conserver controller increases or decreases the threshold pressure in response to regularity of breathing. In one implementation, the conserver controller measures the average breath period and breath period variance over a multiplicity of breaths, and incorporates the regularity of breathing patterns in determining the auto-fire time. In this way, a conserver used by a patient who is exhibiting irregular but detectable breathing patterns will pause for a longer period of time auto-firing; a conserver used by a patient who is breathing regularly until a sudden lapse in detected breath occurs will receive an auto-fired bolus more quickly.

In another aspect, the preferred embodiments of the present invention provide a method of delivering a series of boluses of gas to a patient. The method comprises triggering the delivery of each of a plurality of boluses in accordance with triggering parameters, determining the elapsed time since the last bolus was delivered, and altering the triggering parameters as a function of the elapsed time. In one embodiment, altering the triggering parameters comprises disabling triggering for a blind time. In another embodiment, altering the triggering parameters comprises altering the threshold for triggering. Preferably, altering the threshold for triggering comprises altering a threshold pressure, which can include decreasing the threshold pressure linearly over time or decreasing the threshold pressure asymptotically over a period of time. In certain preferred embodiments, the triggering parameters are a function of the triggering parameters of one or more boluses delivered prior to triggering the delivery. In one implementation, altering the triggering parameters comprises triggering an auto-fire delivery of a bolus when said elapsed time is greater than or equal to a predetermined time. Preferably, the predetermined time is decreased when auto-fire delivery is triggered. In some embodiments, the method further comprises reducing a blind time when auto-fire delivery is triggered.

In yet another aspect, the preferred embodiments of the present invention provide an apparatus for delivering a series of boluses of gas to a patient. The apparatus comprises a gas source, a conserver between the gas source and the patient, a sensor which detects breaths by the patient, and a controller which receives signals from the sensor and triggers a delivery of gas boluses in accordance with predefined triggering parameters. Preferably, the controller determines the time elapsed since the last bolus was triggered, and altering the triggering parameters as a function of the elapsed time. In one embodiment, the triggering parameters comprise a blind period during which the triggering delivery of gas boluses is disabled. In another embodiment, the triggering parameters comprise a threshold inspiratory pressure of the patient. In yet another embodiment, the controller triggers an auto-fire bolus when the elapsed time is greater than a predetermined time. In certain modes, each of the triggering parameters is a function of the triggering parameters of one or more boluses previously delivered.

BRIEF DESCRIPTION OF THE DRAWINGS

FIG. 5 schematically illustrates the system as having a day mode and a night mode of operation;

FIGS. 6A and 6B illustrate different embodiments of the operational mode of FIG. 4;

DETAILED DESCRIPTION OF PREFERRED EMBODIMENTS

Figure 1:
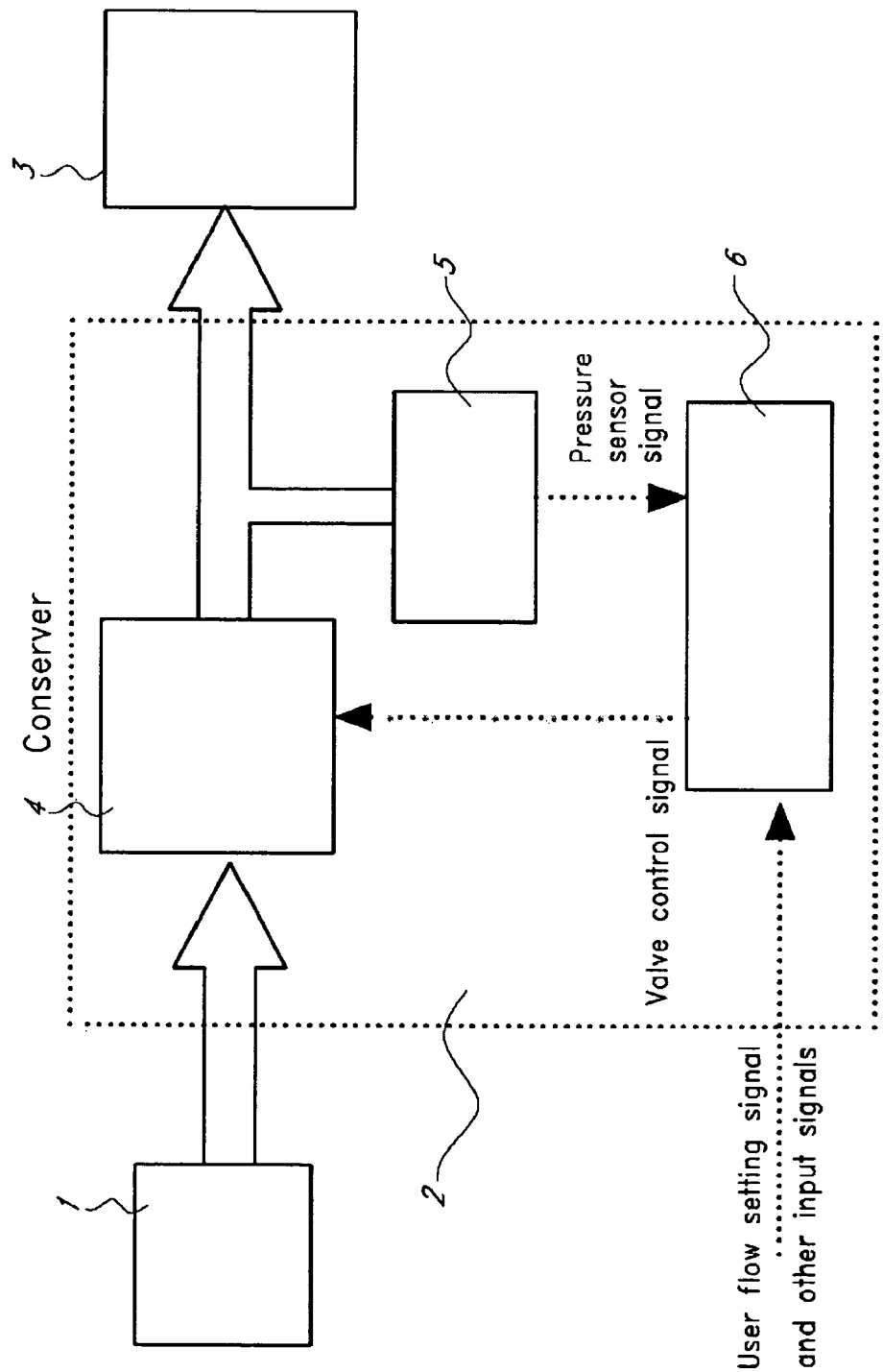
FIG. 1 is a block diagram of a therapeutic gas delivery system according to one preferred embodiment of the present invention.

One preferred embodiment of a therapeutic gas delivery system is illustrated in FIG. 1. The system generally includes an oxygen source 1 and a conserving device 2 for controlling the delivery of the oxygen to a patient 3. The oxygen source 1 can be an oxygen concentrator, high pressure oxygen tank, or any other device that supplies oxygen. The conserving device 2 has a bolus delivery element 4, a breath sensor 5, and a controller 6. The bolus delivery element 4 can include valves of the appropriate type and function. The breath sensor 5 is preferably a breath pressure sensor such as a transducer capable of detecting and measuring inspiratory breath pressure and transmitting signals to the controller 6. The controller 6 includes an electronic circuit and a programmable microprocessor capable of determining the bolus volume and bolus timing based on the signals received from the breath sensor 5. In one implementation, the controller 6 determines the bolus volume by controlling how long the delivery valve 4 is kept open in each delivery and controls the timing of the bolus by determining at which times the valve 4 is opened.

As will be described in greater detail below, the desired functionality of the therapeutic gas delivery system includes the ability to measure inspiratory breath pressure and to control the open timing of the delivery valve, thereby controlling the volume of the bolus. In certain embodiments, the system is configured to address difficulties and problems associated with delivering therapeutic gas to a patient during sleep.

Threshold Pressure Setting

The efficacy of elevating oxygen concentrations in the lungs is generally known to relate to how much oxygen is delivered in early (alveolar) inspiration. While the exact fraction of inspired gas may vary from patient to patient, in general, the bolus volume delivered during the first half of an inspiratory cycle is more significant in oxygenating the patient. Thus, conserving devices are preferably designed to deliver pulses of oxygen to the patient during the very early stages of each inspiratory cycle.

Typically, a conserving device triggers a bolus delivery when it detects a predetermined inspiratory pressure from the breath sensor. Thus, the term "threshold pressure" generally refers to the sensed inspiratory pressure at which a bolus delivery is triggered. In general, it is preferable to set the threshold pressure as high as possible to avoid triggering a bolus delivery based on false breath detection due to electrical signal noise or pressure noise in the cannula caused by patient activities. However, too high a setting can also render the therapy ineffective.

Figure 2:
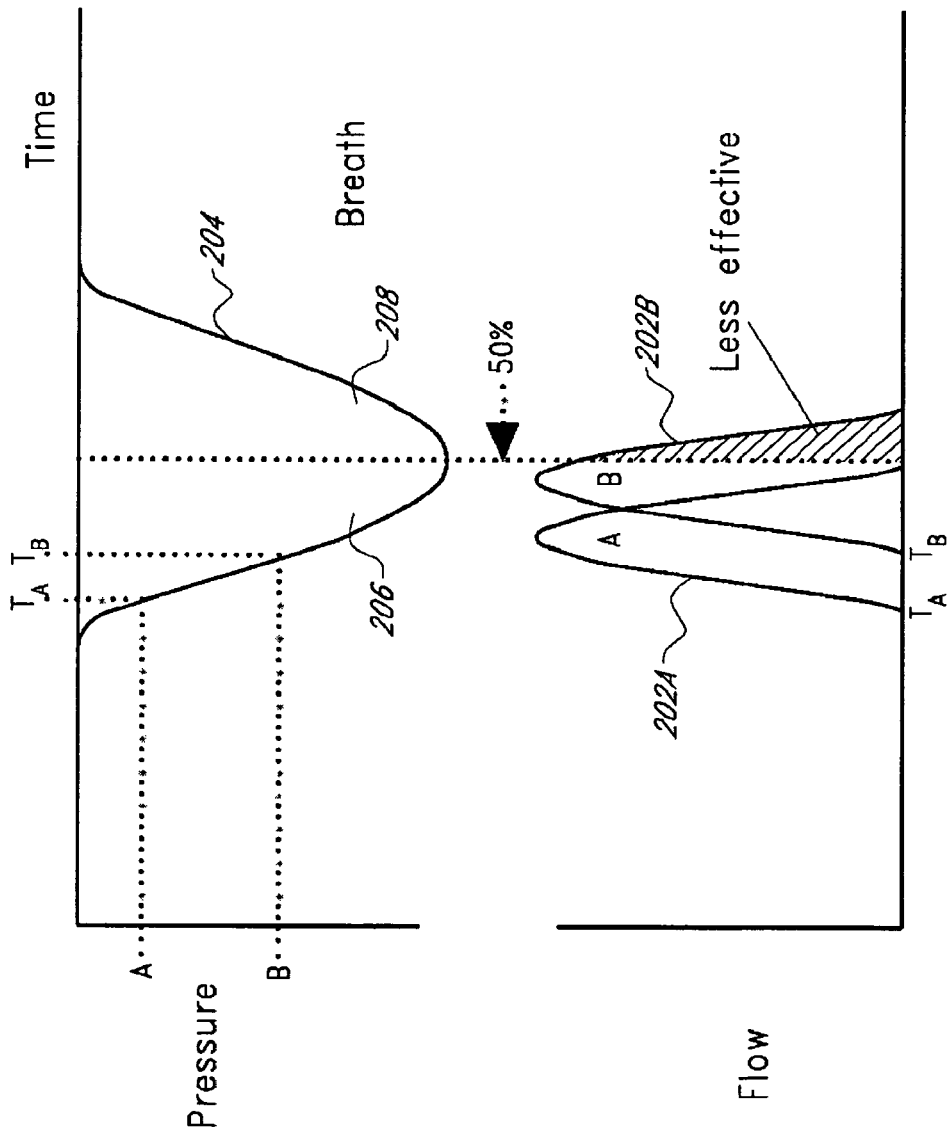
FIG. 2 is a graphic illustration showing the relationship between the timing of a bolus delivery during an inspiratory cycle and the efficacy of the gas delivered.

FIG. 2 is a graphic illustration of the relationship between the threshold pressure setting and the efficacy of the gas delivered. As shown in FIG. 2, the bolus delivery profiles 202A, 202B for two different threshold pressure settings $T_A$ and $T_B$ are correlated to the pressure profile 204 of a patient's inspiratory cycle. Threshold pressure level $T_A$ 202A triggers delivery early enough to allow for full bolus delivery in the first half 206 of the inspiratory cycle. Threshold pressure level $T_B$ 202B, however, causes delivery of a significant portion of the bolus in the second half 208 of the inspiratory cycle, and thus is not as effective. Accordingly, when the threshold pressure level is set too high relatively to the inspiratory pressure of the very early stages of an inspiration cycle, a significant portion of the bolus is likely to be delivered during the second half of the inspiratory cycle which renders the therapy less effective.

Shallow Breathes During Sleep

Figure 3:
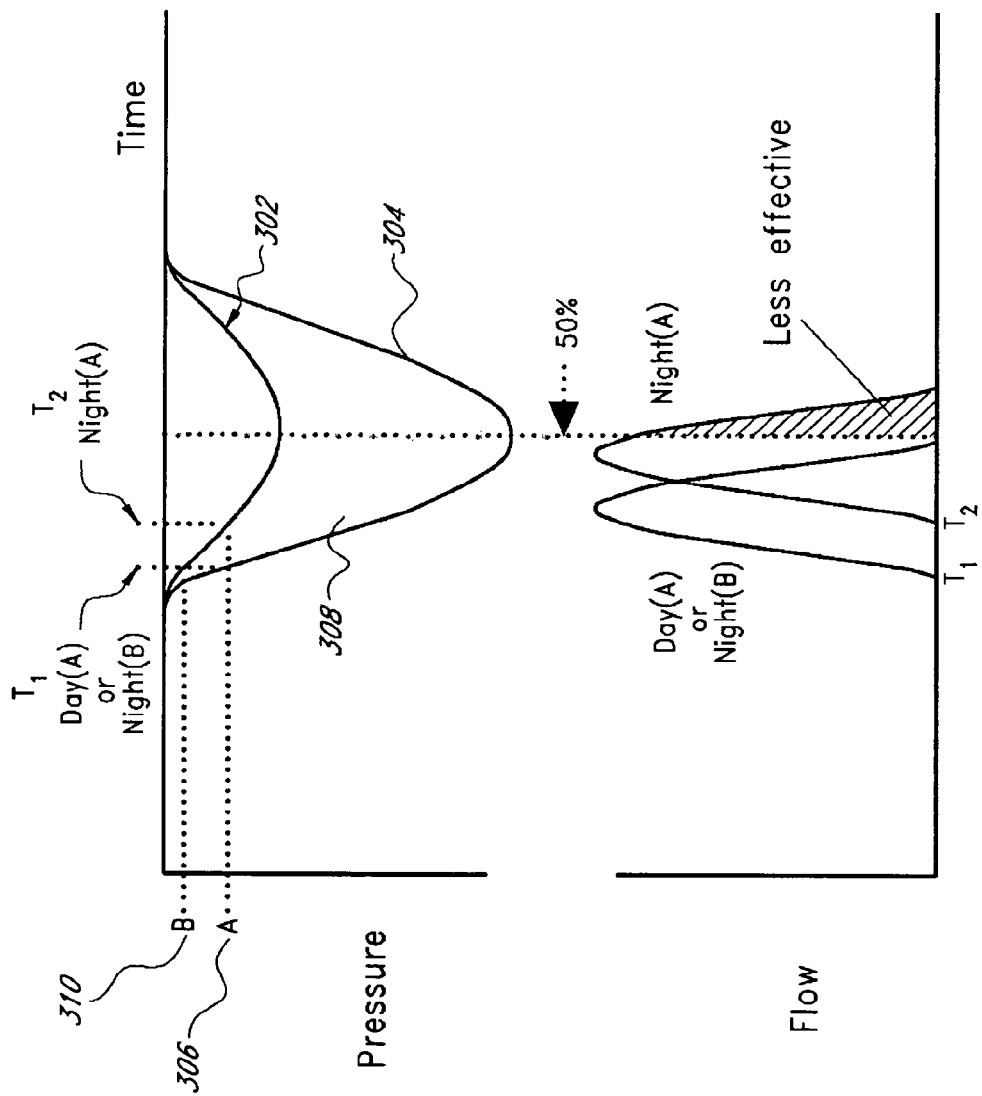
FIG. 3 is a graphic illustration showing the pressure profiles of exemplary inspiratory cycles of a patient's breath during normal activity and during sleep.

Problems associated with high threshold pressure settings are particularly apparent in conventional gas delivery systems when the patient is asleep or in a state of inactivity. As shown in FIG. 3, the inspiratory pressure profile 302 of a patient's breath during sleep may be much shallower than the inspiratory profile 304 of the patient's breath during normal activity. Thus, a threshold pressure value $T_A$ 306, which is effective during normal day activity, may be ineffective at night when the patient's is asleep. During sleep when the breaths are often shallower, the threshold pressure $T_A$ may not be reached sufficiently early in the inspiratory cycle 302 to allow a significant portion of the bolus to be delivered in the first half 308 of the cycle. FIG. 3 shows that a night response to threshold pressure $T_B$ 310 is equivalent to the day response to threshold pressure $T_A$ 306, although it is understood that the night bolus timing and volume do not have to exactly correspond to the day bolus to be effective.

Erratic Breathing During Sleep

Figure 4:
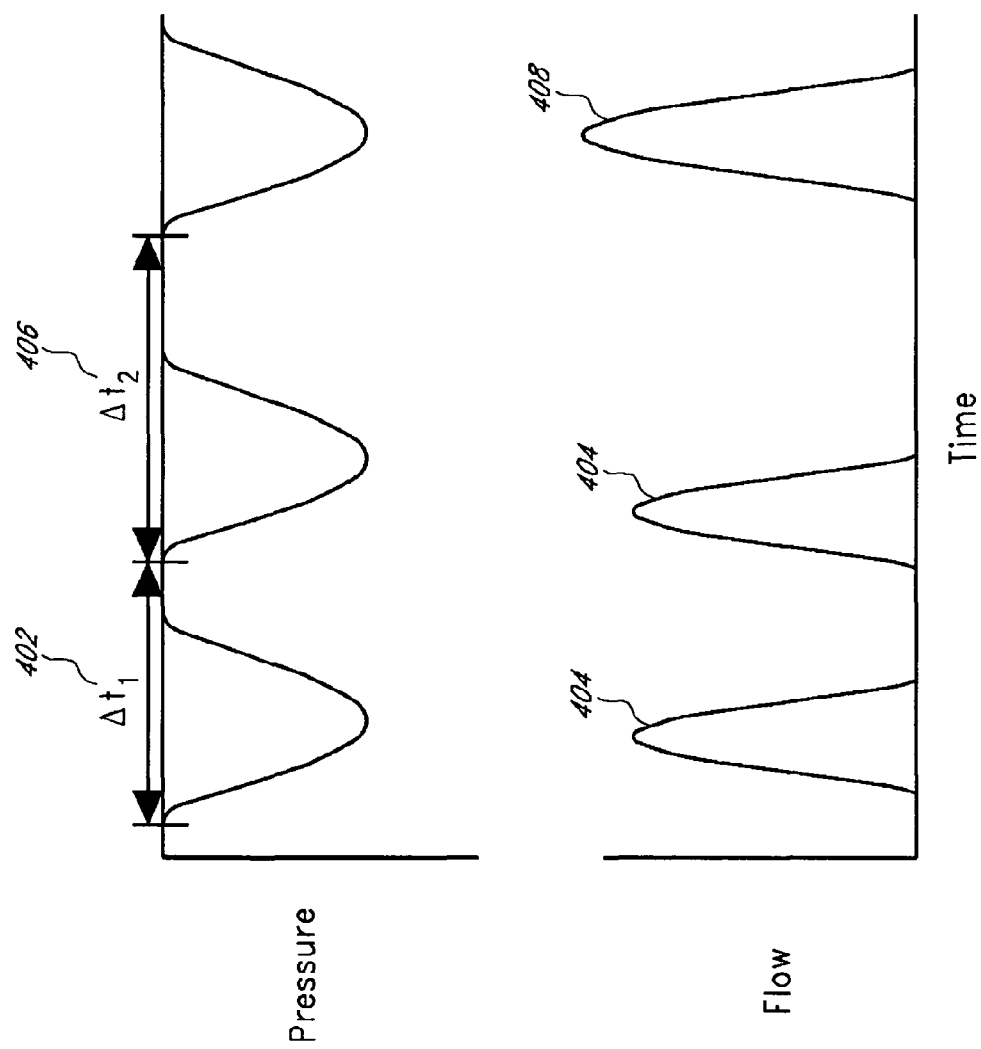
FIG. 4 illustrates a mode of operation of the system of FIG. 1 in which the bolus volume delivered is a function of the elapsed time between successive breaths.

During sleep, breath timing 402, 406 may also be quite erratic. The time elapsed between successive breaths may vary greatly, which makes it difficult for conventional conservers to deliver the prescribed amount of oxygen to the patient over a period of time. In order to keep the overall gas delivered to the patient constant over time, bolus volume 404, 408 may be adjusted as shown in FIG. 4, such that after a longer time 406 between breaths, a larger bolus volume 408 is delivered.

The therapeutic gas delivery systems of the preferred embodiments have features designed to address one or more of the above-described problems typically associated with delivering therapeutic gas to a patient during sleep. This may be particularly important in optimizing the combined system performance of the conserver in concert with the function of the device supplying the gas flow, especially in the case of devices such as oxygen concentrators in which the rate of gas flow delivery is limited by design.

Normal Activity Mode and Sleep Mode Threshold Pressure Settings

In one embodiment, as shown in FIG. 5, the system has settings for switching between a "day" or "normal activity" mode 502 and a "night" or "sleep" mode 504. A lower threshold pressure level or higher sensitivity is preferably used when the patient is sleeping. The bolus is preferably triggered at an earlier time in the inspiratory cycle, allowing for full bolus delivery before the first half of the cycle. Several implementations of this embodiment are possible. The patient may simply be given a user input to the controller, allowing for several different threshold pressure settings or sensitivities, user selectable, to be entered into the controller. The patient may choose a value to be used during normal activity in the day, and change to a lower value to be used at night when the patient is sleeping. Alternatively, either a "day" or "night" mode may be selected, with the sensitivities, A and B programmed into the controller by the patient's caregiver, or loaded at the factory. Although a lower threshold value is more susceptible to false triggers, a sleeping patient is typically quite still and less prone to generate pressure noise in the cannula, which may lead to false triggers. Thus, a higher nighttime sensitivity can be effective, especially if low electrical signal noise can be achieved.

Variable Bolus Volume in Response to Variations in Time Between Breaths

In another embodiment, the system is programmed to vary the bolus volume delivered in response to variations in the elapsed time between breaths, which addresses the erratic breathing pattern concerns described above. As shown in FIG. 6A, the controller can be programmed to measure elapsed time between breaths, $\Delta t$, and apply a control gain G1, thereby delivering a bolus volume such that the average flow rate over time is nearly constant. However, FIG. 6A shows that the bolus volume 602 may become quite large after long periods of elapsed time between breaths. The large boluses may cause discomfort for some patients. Moreover, in a case such as an oxygen concentrator in which the gas supply stores a volume of gas at pressure in an accumulator, large swings in bolus volume can result in swings in the stored pressure in the accumulator. This can be destructive for both the oxygen generation process and for the repeatable delivery of the subsequent bolus, which is driven by the pressure in the accumulator. To address this problem, FIG. 6B shows an alternative embodiment in which a proportional-integral-derivative (PID) algorithm is applied to $\Delta t$ to determine the bolus volume. This has the effect of smoothing out the volume variation while still keeping overall nearly constant flow rate.

Auto-Fire Mode

Figure 7:
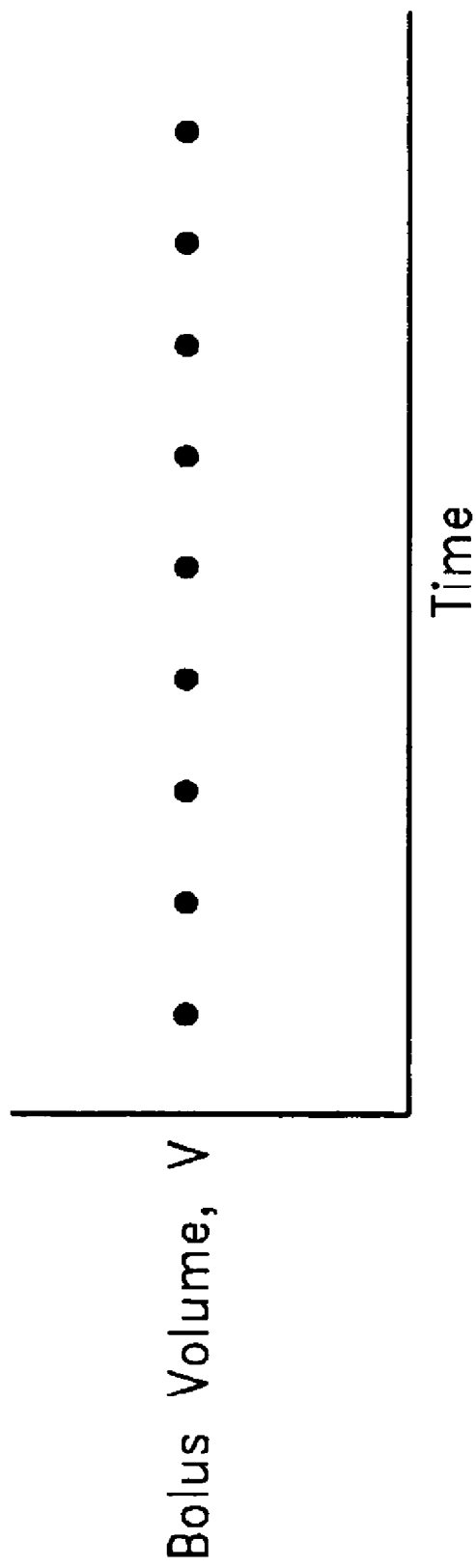
FIG. 7 illustrates an auto-fire mode of operations of the system of FIG. 1.

In yet another embodiment, the system is capable of operating in an auto-fire mode. The term "auto-fire" refers to delivering a constant volume bolus at fixed time intervals independent of the breathing pattern. This feature is particularly effective when breath period and inspiratory pressure profiles are very erratic, or for mouth breathers. As shown in FIG. 7, the controller may be set in a mode in which the conserver simply "auto-fires" a constant volume bolus at a fixed period, not tied to an actual breath. This embodiment relies on the patient entraining oxygen rich air in the cannula into the lungs. If taken to an extreme of very small boluses delivered with no time gap between boluses, this embodiment approaches the performance of a continuous flow device. However, because in this embodiment the gas is delivered in short bursts, more of it penetrates the nasal passages where it can be entrained with inspiration. This allows a smaller overall volume of gas to be delivered.

Adaptive Control Responsive to Multiple Breath Parameters

Figure 8:
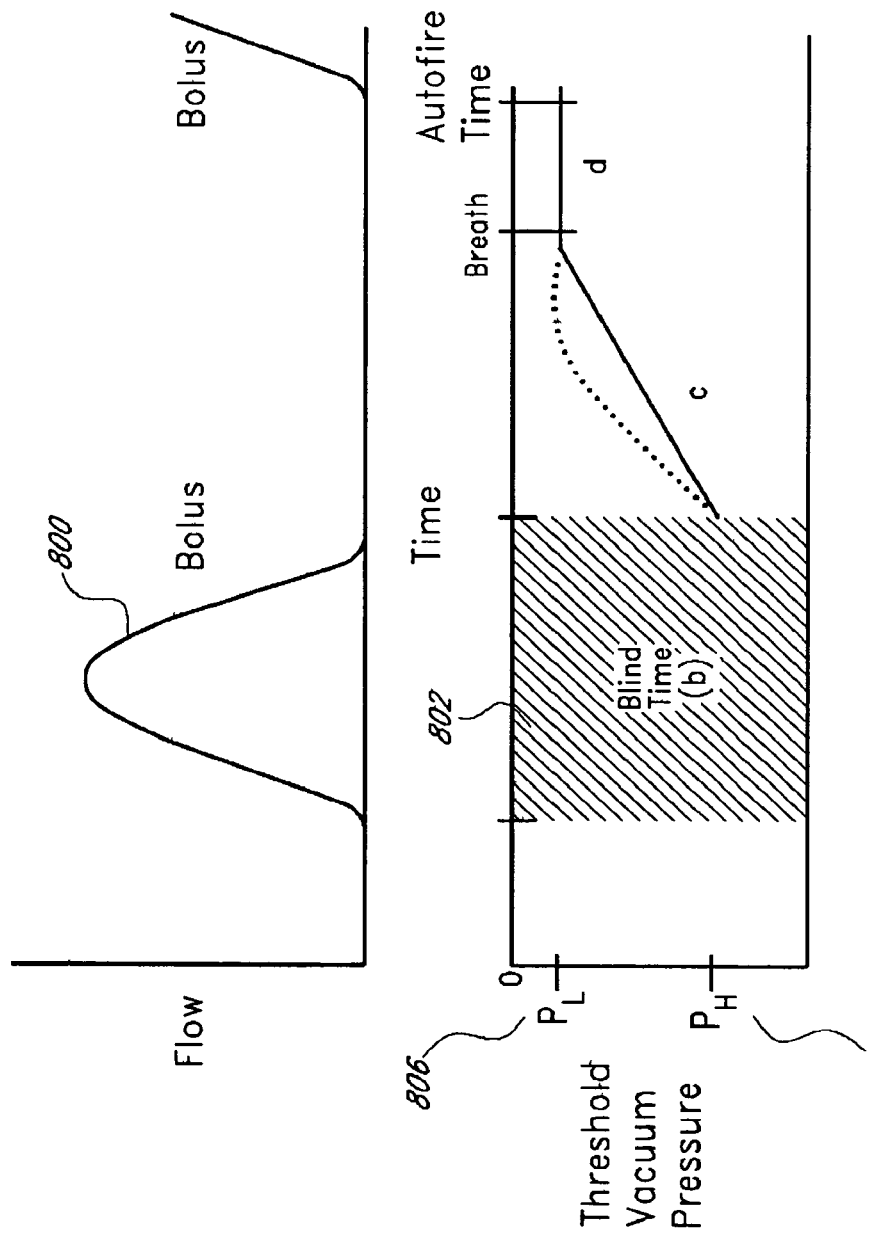
FIG. 8 illustrates an adaptive mode of operations of the system of FIG. 1.

In another embodiment as illustrated in FIG. 8, the system has adaptive controls designed to vary the bolus delivery in response to a number of breath parameters. This feature effectively addresses many of the above issues at the same time, while improving immunity to false, ineffective triggers. As shown in FIG. 8, upon delivery of a bolus 800, the controller enters a "blind time" 802 where it will not accept a breath trigger. The blind time 802 prevents any ineffective bolus delivery for a period of the breath and some period, in the range of about 0.5-3.0 seconds, typically about 1.5 seconds. Upon the end of the blind time 802, the controller sets the trigger sensitivity at a low, noise immune, level, $P_H$ 804. The controller then ramps the trigger sensitivity over a time, typically 1-2 seconds to a higher sensitivity, $P_L$ 806. If after a time, typically about 2-3 seconds after a breath is anticipated, no breath is detected even at the high sensitivity, a bolus is auto-fired. Any suitable curve may be used instead of a linear ramp as shown in FIG. 8. The inventors have found an exponential ramp is effective as well.

As an example of the system of FIG. 8, for a typical oxygen patient breathing about 15 times per minute, a new inspiratory cycle is initiated every 4 seconds. After a bolus is delivered, the conserver spends the next 1.5 seconds blind, during which time all sensor input is ignored. The threshold vacuum pressure may start out at about 0.30 cm of water at that point. Because the anticipated breathing period is 4.0 seconds (calculated from average breathing rates), the threshold pressure is controllably decreased over the next 2.25 seconds (1.5-3.75 seconds from last bolus) until it reaches a higher sensitivity level of about 0.08 cm of water. If, after an additional 2.75 seconds (6.5 seconds from last bolus) no breath has been detected, a bolus is automatically delivered.

Figure 9:
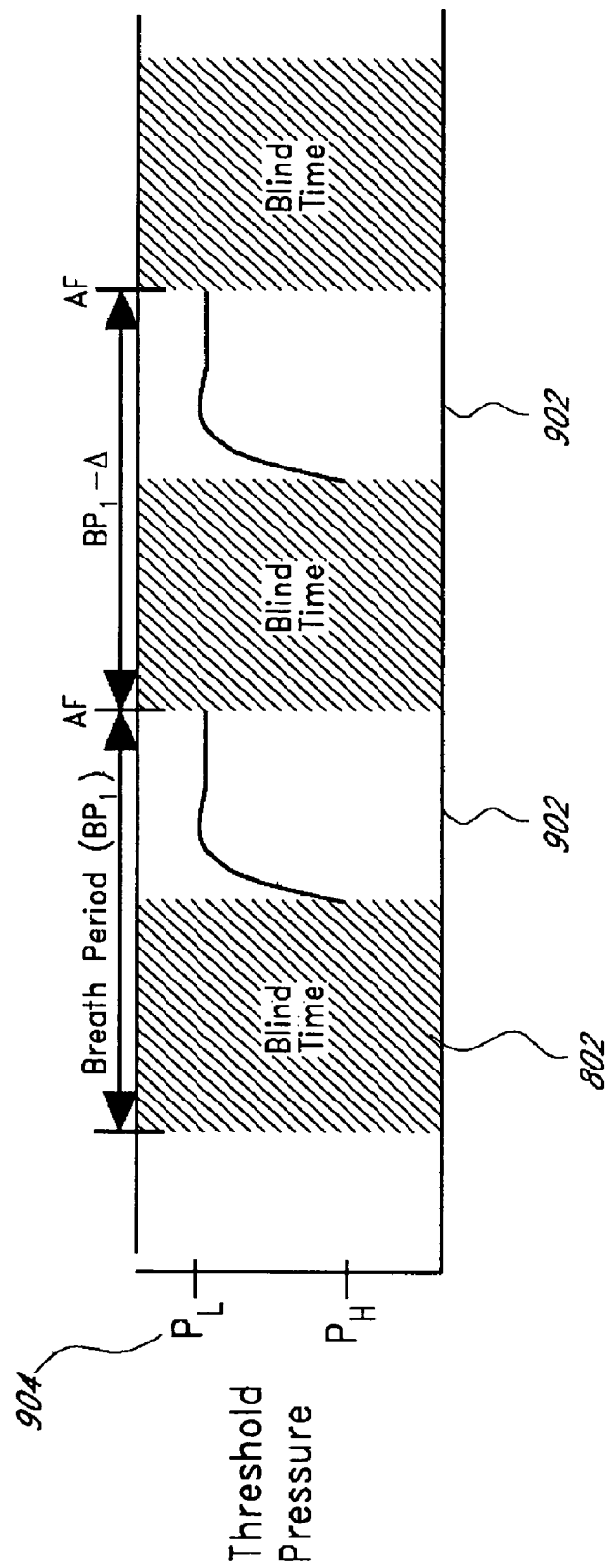
FIG. 9 illustrates another embodiment of the adaptive mode of FIG. 7.

In yet another embodiment as shown in FIG. 9, if an auto-fire event took place on the last cycle, the controller may shorten the time 902 between the end of the blind period 802 to when the auto-fire takes place again. If auto-fire happens on a number of successive cycles, the controller may revert to the fixed auto-fire mode of FIG. 7. The controller may also adjust bolus volume in any of these scenarios to account for variation in breath period. In the event of successive auto-fires, the controller may alternatively be programmed to reduce $P_L$ until reliable breath detection resumes without auto-fires.

Alternatively, the controller may decrease the blind time. If the blind time is decreased, the period during which a breath is detected increases, making it more likely to detect a breath. Decreasing the blind time may be used alone or in concert with reducing $P_L$ 904 to try to return from auto-fire mode to breath detection. In certain embodiments, there is a practical limit to how much the blind time may be decreased which is set by the design of the pressure sensor electronic interface. For example, in an oxygen concentrator design used by the inventors, the sensor interface is zeroed during the blind time. Thus, if the blind time is set too short, the zeroing will not be complete, having the effect of actually reducing the sensitivity of breath detection. In the case of an apnea event, the controller may be programmed to enter continuous auto-fire mode after a predetermined time, and to revert to one of the above modes on set intervals to re-enter normal sleep breathing cycles.

A Method of Determining Bolus Volume and Timing

Figure 10:
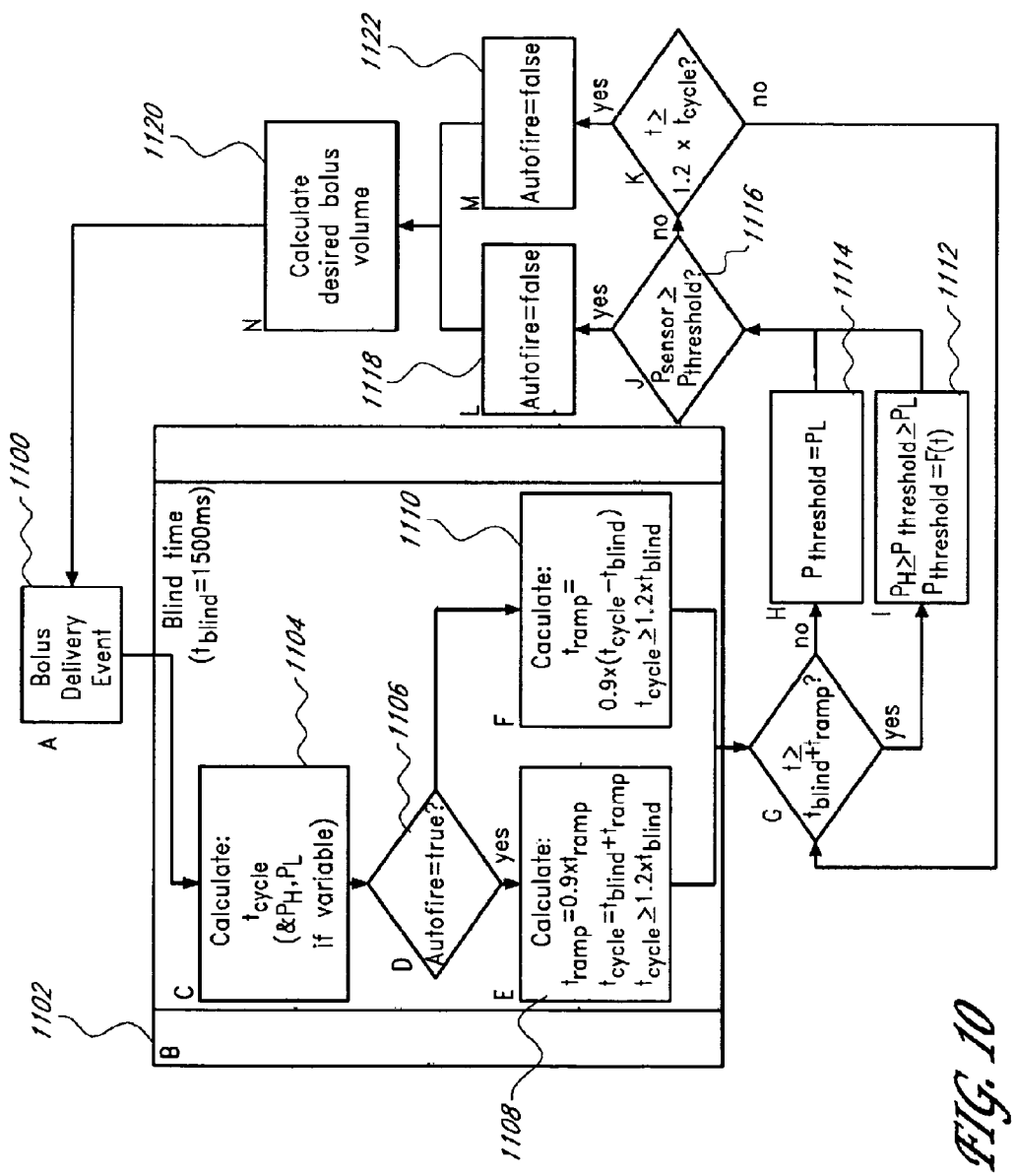
FIG. 10 is a flow chart illustrating a method of delivering a therapeutic gas to patients according to one preferred embodiment of the present invention.

FIG. 10 is a flow chart illustrating a preferred method of determining bolus volume and timing in the delivery of a therapeutic gas to a patient. As shown in FIG. 10, once a bolus is delivered in Step A 1100, the systems enters a blind time $T_{blind}$ of about 1500 ms in step B 1102. During this time, the system performs several computations in Step C 1104, including determining the average breathing cycle time $T_{cycle}$, the appropriate high and low threshold pressure limits, if not fixed, and the time during which the threshold pressure will be reduced, $T_{ramp}$. In Step D 1106, the system determines whether the previous bolus was auto-fired. If it was, then the ramp time is reduced from its previous value in step E 1108. Preferably, in no case is the time before the system auto-fires allowed to encroach on the blind time plus some nominal period, such that for some duration on each breathing cycle a breath may be detected. If the bolus was fired in response to a breath detection, then the ramp period is selected in Step F 1110 such that it is somewhat less than the period between the end of the blind time and the end of the expected breathing cycle ($T_{cycle} - T_{blind}$). This allows a short period before the expected next breath during which the threshold pressure is at its lowest level. Once the blind time passes, the system threshold will be selected as either a decreasing function of time varying between a high and low value in Step I 1112, or as the lowest value in Step H 1114 if the ramp time has passed. The system monitors the pressure signal in Step J 1116, and if a signal that meets the threshold requirements is met, the system fires a bolus in response in Steps L 1118, N 1120, and A 1100. If the signal does not exceed the threshold requirements before some time greater than the expected breathing cycle $T_{cycle}$, then a bolus is automatically triggered in Steps M 1122, N 1120, and A 1100. The cycle then begins again.

Advantageously, the preferred embodiments of the present invention provide a wide range of bolus control options, which can allow a practitioner the flexibility to tailor the bolus delivery patterns to maintain effective therapy for many different types of patient sleep breathing scenarios. These modes may also be useful for daytime operations as well.

Although the foregoing description of the preferred embodiments of the present invention has shown, described and pointed out the fundamental novel features of the invention, it will be understood that various omissions, substitutions, and changes in the form of the details of the invention as illustrated as well the uses thereof, may be made by those skilled in the art, without departing from the spirit of the invention. Consequently, the scope of the invention should not be limited to the foregoing discussions.

What is claimed is:

1. A system for delivering therapeutic breathing gas to a patient, comprising:
    a gas source;
    a conserver between the gas source and the patient;
    a sensor for detecting patient breath events and measuring the parameters of the breath events, said parameters including breath pressure level;
    processor and control elements for acquiring signals from the sensor and controlling the delivery of gas to the patient, wherein the system supports at least one mode of operation such that a threshold breath pressure level detected by the sensor, which causes the processor and control elements to deliver a volume of gas to the patient, may be user selectable such that the volume of gas is delivered to the patient when the patient's threshold breath pressure level is at the level selected by the user; and
    wherein the system provides a plurality of user selectable threshold pressure levels, said threshold pressure levels comprising a lower level adapted to trigger delivery of gas to the user when the user is asleep or in a state of inactivity such that the user's breath is shallower than normal.

2. The system of claim 1, wherein the different levels of threshold breath pressure comprise two user-selectable levels, representing a night mode and a day mode, and the actual values of each level are determined by the patient's caregiver.

3. The system of claim 1, wherein the gas is oxygen and the gas source is an oxygen concentrator.

4. A system for delivering therapeutic breathing gas to a patient, comprising:
    a gas source;
    a conserver between the gas source and the patient;
    a sensor for detecting patient breath events and measuring the parameters of the breath events such as breath pressure level; and
    processor and control elements for acquiring signals from the sensor and controlling the delivery of gas to the patient, wherein the system supports at least one auto-fire mode of operation such that the processor and control elements measure the time since the last breath detected by the sensor, and if no breath is detected after a predetermined time period and no gas is delivered to the patient in this predetermined time period, a volume of gas is delivered to the patient automatically.

5. The system of claim 4, wherein after the automatic delivery of the volume of gas, the processor reduces the breath pressure level which will trigger bolus delivery for the next breath cycle.

6. The system of claim 4, wherein the processor reduces the breath period for the next breath cycle.

7. The system of claim 4, wherein the gas is oxygen and the gas source is an oxygen concentrator.

8. An apparatus for delivering a series of boluses of gas to a patient, comprising:
    a gas source;
    a conserver between the gas source and the patient;
    a sensor which detects breaths by the patient; and
    a controller which receives signals from the sensor and triggers delivery of gas boluses in accordance with predefined triggering parameters, said controller determining the time elapsed since the last bolus was triggered, and altering the triggering parameters as a function of said elapsed time.

9. The apparatus of claim 8, wherein said triggering parameters comprise a blind period during which said triggering delivery of gas boluses is disabled.

10. The apparatus of claim 8, wherein said triggering parameters comprises a threshold inspiratory pressure of the patient.

11. The apparatus of claim 8, wherein the controller triggers an auto-fire bolus when said elapsed time is greater than a predetermined time.

12. The apparatus of claim 8, wherein each of the said triggering parameters is a function of the triggering parameters of one or more boluses previously delivered.

* * * * *

US007841343C1

(12) INTER PARTES REEXAMINATION CERTIFICATE (1210th)
United States Patent
Deane et al.

(10) Number: US 7,841,343 C1
(45) Certificate Issued: Dec. 7, 2015

(54) SYSTEMS AND METHODS FOR DELIVERING THERAPEUTIC GAS TO PATIENTS

(75) Inventors: Geoffrey Frank Deane, Goleta, CA (US); Brenton Alan Taylor, Kenwood, CA (US)

(73) Assignee: INOGEN, INC., Goleta, CA (US)

Reexamination Request:
  No. 95/001,885, Mar. 1, 2012

Reexamination Certificate for:
  Patent No.: 7,841,343
  Issued: Nov. 30, 2010
  Appl. No.: 11/147,409
  Filed: Jun. 6, 2005

Related U.S. Application Data

(60) Provisional application No. 60/577,088, filed on Jun. 4, 2004.

(51) Int. Cl.
  *A61M 11/00* (2006.01)
  *A61M 16/10* (2006.01)
  *A61M 16/06* (2006.01)
  *A61M 16/00* (2006.01)

(52) U.S. Cl.
  CPC .......... *A61M 16/10* (2013.01); *A61M 16/0677* (2014.02); *A61M 16/101* (2014.02); *A61M 2016/0021* (2013.01)

(58) Field of Classification Search
  None
  See application file for complete search history.

(56) References Cited

To view the complete listing of prior art documents cited during the proceeding for Reexamination Control Number 95/001,885, please refer to the USPTO's public Patent Application Information Retrieval (PAIR) system under the Display References tab.

*Primary Examiner* — Peter C English

(57) ABSTRACT

A system for delivering therapeutic breathing gas to patients is provided to deliver a variable bolus volume in response to the patient's breathing pattern. The system includes a gas source, a conserver between the gas source and the patient, a sensor which detects breaths by the patient and a controller which receives signals from the sensor and triggers delivery of gas boluses in accordance with predefined triggering parameters, with the controller determining the time elapsed since the last bolus was triggered and altering the triggering parameters as a function of the elapsed time.

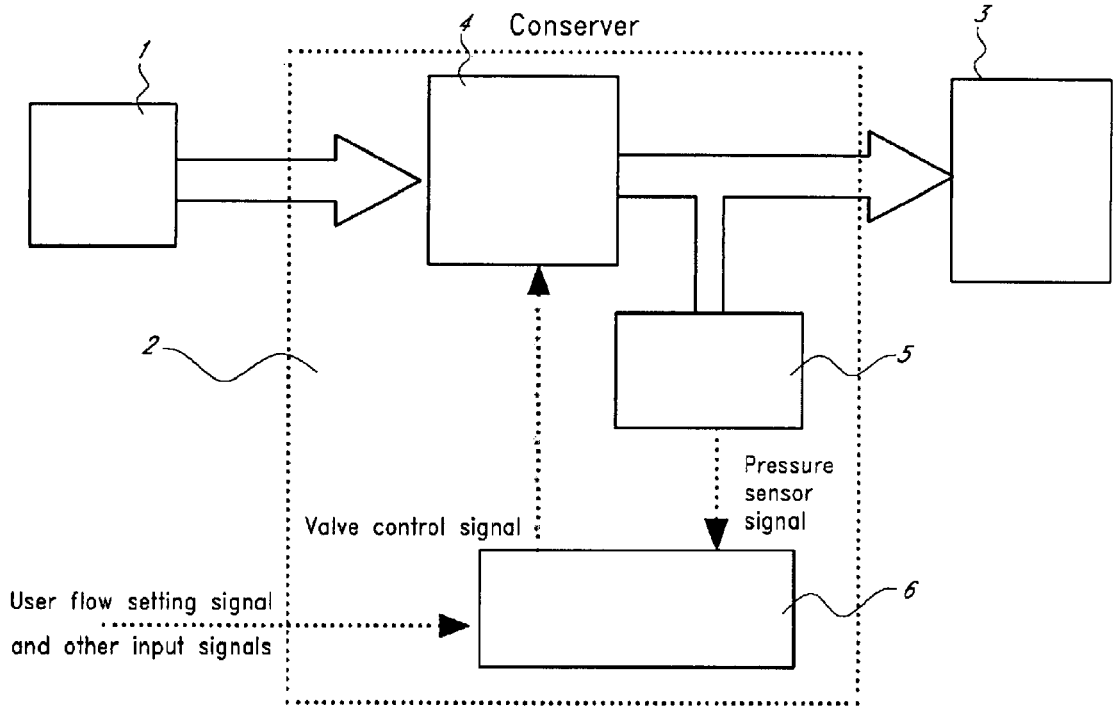

INTER PARTES REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-3 is confirmed.

Claims 4 and 7 are cancelled.

Claims 5, 6, 8 and 10 are determined to be patentable as amended.

Claims 9, 11 and 12, dependent on an amended claim, are determined to be patentable.

New claims 13-17 are added and determined to be patentable.

5. [The system of claim 4,] *A system for delivering therapeutic breathing gas to a patient, comprising:*

*a gas source;*

*a conserver between the gas source and the patient;*

*a sensor for detecting patient breath events and measuring the parameters of the breath events such as breath pressure level;*

*and processor and control elements for acquiring signals from the sensor and controlling the delivery of gas to the patient, wherein the system supports at least one auto-fire mode of operation such that the processor and control elements measure the time since the last breath detected by the sensor, and if no breath is detected after a predetermined time period and no gas is delivered to the patient in this predetermined time period, a volume of gas is delivered to the patient automatically, wherein after the automatic delivery of the volume of gas, the processor reduces the breath pressure level which will trigger bolus delivery for the next breath cycle.*

6. [The system of claim 4] *A system for delivering therapeutic breathing gas to patient, comprising:*

*a gas source;*

*a conserver between the gas source and the patient;*

*a sensor for detecting patient breath events and measuring the parameters of the breath events such as breath pressure level;*

*and processor and control elements for acquiring signals from the sensor and controlling the delivery of gas to the patient, wherein the system supports at least one auto-fire mode of operation such that the processor and control elements measure the time since the last breath detected in the sensor, and if no breath is detected after a predetermined time period and no gas is delivered to the patient in this predetermined time period, a volume of gas delivered to the patient automatically, wherein the processor reduces the breath period for the next breath cycle.*

8. An apparatus for delivering a series of boluses of gas to a patient, comprising:

a gas source;

a conserver between the gas source and the patient;

a sensor which detects breaths by the patient; and a controller which receives signals from the sensor and triggers delivery of gas boluses in accordance with pre-defined triggering parameters, said controller determining the time elapsed since the last bolus was triggered, and altering the triggering parameters as a function of said elapsed time, *said triggering parameters comprising a threshold inspiratory pressure level, wherein altering the triggering parameters comprises changing the threshold inspiratory pressure level so that delivery of a gas bolus can be triggered in response to a lower inspiratory pressure.*

10. The apparatus of claim 8, wherein *altering* said triggering parameters comprises [a] *lowering the* threshold inspiratory pressure of the patient *linearly over time*.

*13. The system of claim 1, wherein the system provides a plurality of pre-set discrete threshold pressure levels.*

*14. The system of claim 1 further comprising a user interface, said user interface configured to allow the patient to switch between the pre-set discrete threshold pressure levels.*

*15. The system of claim 1, wherein the system supports at least one mode of operation such that the processor automatically switches the threshold pressure level from a higher level to the lower level if no breath is detected for a predetermined time period.*

*16. The system of claim 15, wherein the threshold pressure level is controllably decreased from the higher level to the lower level over a time interval.*

*17. The system of claim 15, wherein a volume of as is automatically delivered to the patient if no breath is detected for an additional predetermined time period after the threshold pressure level is decreased to the lower level.*

\* \* \* \* \*